United States Patent
Gauckler et al.

(10) Patent No.: US 8,975,301 B2
(45) Date of Patent: Mar. 10, 2015

(54) ULTRASTABLE PARTICLE-STABILIZED FOAMS AND EMULSIONS

(75) Inventors: Ludwig J. Gauckler, Zurich (CH); Andre R. Studart, Zurich (CH); Elena Tervoort, Zurich (CH); Urs T. Gonzenbach, Zurich (CH); Ilke Akartuna, Zurich (CH)

(73) Assignee: ETH Zurich, Zurich (CH)

( * ) Notice: Subject to any disclaimer, the term of this patent is extended or adjusted under 35 U.S.C. 154(b) by 1769 days.

(21) Appl. No.: 12/097,199

(22) PCT Filed: Dec. 12, 2005

(86) PCT No.: PCT/CH2005/000744
§ 371 (c)(1),
(2), (4) Date: Oct. 31, 2008

(87) PCT Pub. No.: WO2007/068127
PCT Pub. Date: Jun. 21, 2007

(65) Prior Publication Data
US 2009/0325780 A1   Dec. 31, 2009

(51) Int. Cl.
*B01F 3/04* (2006.01)
*B01J 13/02* (2006.01)
(Continued)

(52) U.S. Cl.
CPC ............. *B01J 13/02* (2013.01); *A23L 1/0097* (2013.01); *A61L 27/105* (2013.01); *A61L 27/56* (2013.01); *A62D 1/0071* (2013.01); *B82Y 30/00* (2013.01); *C01B 13/145* (2013.01); *C01B 21/06* (2013.01); *C01F 7/023* (2013.01); *C01F 7/026* (2013.01); *C01F 17/0043* (2013.01); *C04B 35/6263* (2013.01); *C04B 35/632* (2013.01); *C04B 38/106* (2013.01); *C01P 2004/02* (2013.01); *C01P 2004/10* (2013.01); *C01P 2004/64* (2013.01); *C01P 2006/12* (2013.01); *C01P 2006/22* (2013.01); *C04B 2103/48* (2013.01); *C04B 2111/00793* (2013.01); *C04B 2111/0081* (2013.01); *C04B 2235/3212* (2013.01); *C04B 2235/3217* (2013.01); *C04B 2235/3224* (2013.01); *C04B 2235/3229* (2013.01); *C04B 2235/3244* (2013.01); *C04B 2235/3286* (2013.01); *C04B 2235/3418* (2013.01);
(Continued)

(58) Field of Classification Search
None
See application file for complete search history.

(56) References Cited

U.S. PATENT DOCUMENTS 3,041,190 A    6/1962 Griffith et al.
3,326,691 A    6/1967 Moore
(Continued)

OTHER PUBLICATIONS

Binks, Bernard, Particles as surfactants—similarities and differences, 2002, Current Opinion in Colloid & Interface Science, 7, pp. 21-41.*

(Continued)

*Primary Examiner* — Melvin C Mayes
*Assistant Examiner* — Stefanie Cohen
(74) *Attorney, Agent, or Firm* — Marshall, Gerstein & Borun LLP

(57) ABSTRACT

Described is a method to prepare wet foams exhibiting long-term stability wherein colloidal particles are used to stabilize the gas-liquid interface, said particles being initially inherently partially lyophobic particles or partially lyophobized particles having mean particle sizes from 1 nm to 20 μm. In one aspect, the partially lyophobized particles are prepared in-situ by treating initially hydrophilic particles with amphiphilic molecules of specific solubility in the liquid phase of the suspension.

16 Claims, 5 Drawing Sheets

(51) Int. Cl.
| | |
|---|---|
| A23L 1/00 | (2006.01) |
| A61L 27/10 | (2006.01) |
| A61L 27/56 | (2006.01) |
| A62D 1/02 | (2006.01) |
| B82Y 30/00 | (2011.01) |
| C01B 13/14 | (2006.01) |
| C01B 21/06 | (2006.01) |
| C01F 7/02 | (2006.01) |
| C01F 17/00 | (2006.01) |
| C04B 35/626 | (2006.01) |
| C04B 35/632 | (2006.01) |
| C04B 38/10 | (2006.01) |
| C04B 103/48 | (2006.01) |
| C04B 111/00 | (2006.01) |

(52) U.S. Cl.
CPC ... *C04B2235/441* (2013.01); *C04B 2235/5409* (2013.01); *C04B 2235/5445* (2013.01); *C04B 2235/77* (2013.01); *C04B 2235/96* (2013.01); *C04B 2235/9607* (2013.01)
USPC .......................................................... 516/10

(56) References Cited

U.S. PATENT DOCUMENTS

| | | | |
|---|---|---|---|
| 3,554,907 A | | 1/1971 | Moore, Jr. |
| 4,552,708 A | * | 11/1985 | Kimura et al. .................. 264/53 |
| 5,006,405 A | * | 4/1991 | Watkins et al. ................ 428/323 |
| 5,472,493 A | * | 12/1995 | Regan ........................... 106/491 |

OTHER PUBLICATIONS

Dickinson et al., Factors Controlling the Formation and Stability of Air Bubbles Stabilized by Partially Hydrophobic Silica Nanoparticles, 2004, Langmuir, 20, pp. 8517-8525.*
Alargova et al., "Foam Superstabilization by Polymer Microrods," *Langmuir* 2004, 20 (24), 10371-10374.
Ametov et al., "Hydrophobic Interactions in Concentrated Colloidal Suspensions: A Rheological Investigation," *J. Phys. Chem B* 2004, 108, 12116-12122.
Aveyard et al., "Emulsions stabilized solely by colloidal particles," *Advances in Collloid and Interface Science*, 100-102, 2003, 503-546.
Binks et al., "Particles as surfactants—similarities and differences," *Current Opinion in Colloid and Interface Science* 7(2002), 21-41.
Brooker, B,.E., "The Stabilisation of Air in Foods Containing Fat—A Review," *Food Structure* 12 (1993), 115-122.
Christenson et al., "Direct measurements of the force between hydrophobic surfaces in water," *Advances in Colloid and Interface Science* 91 (2001), 391-436.
Dickinson et al., "Factors Controlling the Formation and Stability of Air Bubbles Stabilized by Partially Hydrophobic Silica Nanopartices," *Langmuir* 2004, 20, 8517-8525.
Dinsmore et al., "Colloidosomes: Selectively Permeable Capsules Composed of Colloidal Particles," *Science 298* (Nov. 1, 2002) 1006-1009.
Du et al., "Outstanding Stability of Particle-Stabilized Bubbles," *Langmuir 2003*, 19, 3106-3108.
Goff, H.D., "Colloidal Aspects of Ice Cream—A Review," *Int. Dairy Journal 7* (1997) 363-373.
Green et al., "Cellular Ceramics: Intriguing Structures, Novel Properties, and Innovative Applications," *MRS Bulletin* Apr. 2003, 2300. 96-.
Griffith et al., "Tissue Engineering—Current Challenges and Expanding Opportunities," *Science 295*, (2002) 1009-1014.
Hench, L.L., "Bioceramics," *J. Am. Ceram. Soc., 81* (7)1998, 1705-1728.
Hench et al., "Third—Generation Biomedical Materials," *Science 295*, Feb. 8, 2002, 1014-1017.
Hidber et al., "Influence of the Dispersant Structure on Properties of Electrostatically Stabilized Aqueous Alumina Suspensions," *Journal of the European Ceramic Society, 17*(2), 1997, 239-249.
Israelachvili, et al., "The Hydrophobic Interaction is long range, decaying exponentially with distance," *Letters to Nature*, Nov. 25, 1982.
Kam et al., "Anomalous Capillary Pressure, Stress, and Stability of Solids-Coated Bubbles," *Journal of Colloid and Interface Science*, 213, 329-339 (1999).
Kaptay, G., "Interfacial criteria for stabilization of liquid foams by solid particles," *Colloids and Surfaces A: Physicochem Eng. Aspects 230* (2004) , 67-80.
Murray, et al., "Foam stability: proteins and nanoparticles," *Current Opinion in Colloid and Interface Science 9* (2004) 314-320.
Moudgil, et al., "Surface Chemistry in Dispersion, Flocculation and Flotation," Chapter 10 in *Handbook of Applied Surface and Colloid Chemistry*, ed. K. Holmber., John Wiley & Sons, Ltd., 2001.
Nikolaides et al., "Electric-field induced capillary attraction between like-charged particles at liquid interfaces," *Nature 420* Nov. 21, 2002, 299-301.
Padture et al., "Thermal Barrier Coatings for Gas-Turbine Engine Applications," *Science 296*, Apr. 12, 2002, 280-284.
Parker, et al., "Bubbles, Cavities and the Long-Ranger Attraction between Hydrophobic Surfaces," *J. Phys. Chem.* 1994, 98, 8468-8480.
Simone et al., "Aluminum Foams Produced by Liquid-State Processes," *Acta mater 46* (9), 3109-3123, 1998.
Sun et al., "The Optimum Wetting Angle for the Stabilization of Liquid-Metal Foams by Ceramic Particles: Experimental Simulations," *Metallurgical and Materials Transactions 33A*, Oct. 2002, 3285-3292.
International Search Report in corresponding PCT/CH2005/000744, Dec. 13, 2006.

* cited by examiner

ULTRASTABLE PARTICLE-STABILIZED FOAMS AND EMULSIONS

TECHNICAL FIELD

The present invention belongs to the field of foam formation, in particular to the field of stable foam formation.

BACKGROUND ART

The long-term stability of foams is an essential requirement in a wide number of applications ranging from food and cosmetics to biomedical implants and engineering low-weight structures. Foams are extensively used as an end product in food and cosmetics, where the long-term stability is essential to keep desired physical and chemical properties such as texture and rheological behavior [1, 2]. Well-established and emerging applications that use foams as an intermediate structure to produce macroporous materials are also widely spread in the engineering field to fabricate thermal insulating materials and low-weight structures [3-5], as well as in medicine to produce artificial implants and scaffolds for drug delivery and tissue engineering [6, 7]. As an intermediate material, the foam has to be stable enough to allow for the fabrication of structures with tailored porosity and pore size distribution.

However, foams are inherently thermodynamic unstable systems which tend to undergo rapid coalescence and disproportionation of bubbles, due to the markedly high interfacial energy associated with the gas-liquid interface.

The state-of-the-art method to inhibit the coalescence and disproportionation of bubbles in a foam is to use biomolecules (e.g. proteins and lipids) or long-chain surfactants (e.g. soaps and detergents), which adsorb at the gas-liquid interface reducing the foam overall free energy. However, since the adsorption of these molecules at the interface is most often a reversible process, no long-term stability can be achieved by this means. A practical solution to this problem has been the use of gelling agents to set the foam structure before coalescence and disproportionation takes place. This has also been accomplished by solidifying the foam liquid media (lamellas). Most of such setting processes are triggered by temperature changes, which limit the fixing mechanism to relatively thinned cross-sections where no significant temperature gradients are developed. Alternative setting mechanisms based solely on chemical reactions at the foam liquid media are also possible, but are either very specific for a given foam system and contain often toxic reactants.

Thus, there exists still a need for foams with improved long-time stability as well as means suitable to achieve such long-lasting foams.

In addition to surface active molecules, it was only recently recognized that partially-hydrophobic particles can also stabilize air bubbles in surfactant-free diluted suspensions [8-14]. Similarly to surfactant molecules, the adsorption of colloidal particles onto a gas bubble surface lowers the overall free energy of the gas-liquid interface. The reduction of the total free energy upon particle adsorption is achieved by replacing part of the gas-liquid interfacial area with solids, rather than reducing the interface tension as in the case of surfactant molecules [8, 9, 14]. The wetting properties of the adsorbing particle determine its position at the interface and therefore the amount of total gas-liquid interfacial area replaced. Particles exhibiting intermediate hydrophobicity (contact angle $\theta$ close to 90°) can replace a large area of the gas-liquid interface and thus are the most efficient in reducing the overall interfacial free energy. However, the interfacial adsorption of submicron-sized particles displaying contact angles as low as 20° can already reduce the interface free energy by more than a few hundred kTs, implying that particles are irreversibly adsorbed at the air-water interface even for slightly lyophobized particle surfaces [14].

The stabilization of air bubbles with partially lyophobic particles alone has been so far restricted to model experiments and to a few observations of single air bubbles on thin top layers in diluted suspensions [8, 9, 14].

DISCLOSURE OF THE INVENTION

Hence, it is a general object of the invention to provide a simple, general and preferably also inexpensive method to prepare wet foams, in particular high-volume wet foams, exhibiting unprecedented long-term stability wherein the whole of the suspension is homogeneously foamed.

It is another object to provide means for preparing long-term stable foams.

Now, in order to implement these and still further objects of the invention which will become more readily apparent as the description proceeds, the method to prepare wet foams exhibiting long-term stability is manifested by the features that colloidal particles in a suspension are used to stabilize the gas-liquid interface, said particles being present in amounts of at least about 1% v/v referred to the volume of the suspension, and the whole of said suspension being homogeneously foamed.

The particles used to stabilize the gas-liquid interface are partially lyophobic or lyophobized or their behavior is accordingly tuned by changing the properties of the liquid media.

Long-time stability as used herein, in general means at least 30 minutes, preferably 2 days, more preferred 1 week, whereby wet foams of the present invention can have stabilities of up to one year or more.

The terms lyophobic and lyophobized as used here designates particles that are hydrophobic and hydrophobized, respectively, and particles that are metal melt repelling in case of metal foams.

The terms hydrophobic as used herein means miscible with water in amounts of up to 1% v/v referred to the total volume of the mixture.

The term hydrophilic in particular includes e.g alcohols and glycols.

The terms partially lyophobic particles, partially lyophobized particles, partially hydrophobic particles and partially hydrophobized particles herein are used for particles obtained by initially hydrophobic/lyophobic particles that have been partially hydrophilized/lyophilized and initially hydrophilic/lyophilic particles that have been partially hydrophobized/lyophobized.

Where aqueous systems are concerned, the terms lyophilic, lyophilized, lyophobic, lyophobized are used synonymous to hydrophilic, hydrophilized, hydrophobic, hydrophobized.

The partial lyophobization can be achieved in different ways, namely
- by treating a hydrophilic surface with a specific amphiphilic molecule,
- rendering the behavior of hydrophobic particles more hydrophilic by tuning the hydrophilicity of the solvent of the suspension to be foamed,
- by treating a hydrophobic surface with a specific amphiphilic molecule The high stability achieved with this new method stems from the irreversible nature of the adsorption of said partially-lyophobic or partially-lyophobized particles at the bubble surface. The stabilizing colloidal particles are e.g. initially hydrophilic and, preferably in-situ, partially hydrophobized through the adsorption of specific amphiphilic molecules on the particle surface.

As a general rule, the specific amphiphilic molecules used to in-situ partially hydrophobize initially hydrophilic particles should be able to reduce the surface tension of an air-water interface to values lower or equal than 65 mN/m for concentrations lower or equal than 0.5 mol/l and have a solubility in the liquid phase of the suspension given by the following equation:

$$\text{SOLUBILITY[mol/l]} \geq m \cdot \frac{\phi}{1-\phi} \cdot \rho_{powder} \cdot S_A$$

$m = 4 \cdot 10^{-8} \, [\text{mol/m}^2]$ $\phi$: Solids Loading [−]

$\rho_{powder}$: Density of powder [g/l]

$S_A$: Surface Area of Powder [m²/g]

The amphiphilic molecules consist of a tail (designated below as R) coupled to a headgroup. The tail can be aliphatic (linear or branched) or cyclic (alicyclic or aromatic) and can carry substituents. Such substituents are e.g. —$C_nH_{2n+1}$ with n<8, —OH, —$NH_3$, etc. Preferred tails are optionally substituted linear carbon chains of 2 to 8 carbon atoms. The headgroups that are coupled to the tail preferably are ionic groups. Examples of possible headgroups are specified in Table 1 below, wherein the tail is designated as R.

For hydrophilization of initially hydrophobic particles, the amphiphilic molecules suitable for in-situ surface hydrophilization have a critical micelle concentration (CMC) higher than 10 μmol/l and/or they have a solubility higher than 1 μmol/l.

TABLE 1

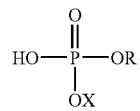

phosphates
X: H, $C_nH_{2n+1}$
(n < 7), alkaline metals

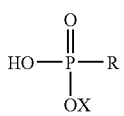

phosphonates
X: H, $C_nH_{2n+1}$
(n < 7), alkaline metals

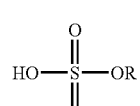

sulfates

TABLE 1-continued

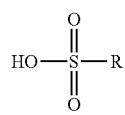

sulfonates
R—OH
alcohols

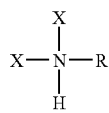

amines
X: H, $C_nH_{2n+1}$
(n < 7)

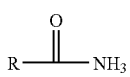

amides

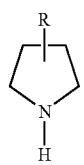

pyrrolidines

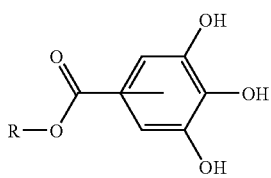

gallates

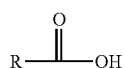

carboxylic acids
or corresponding salts.
Some preferred examples are:

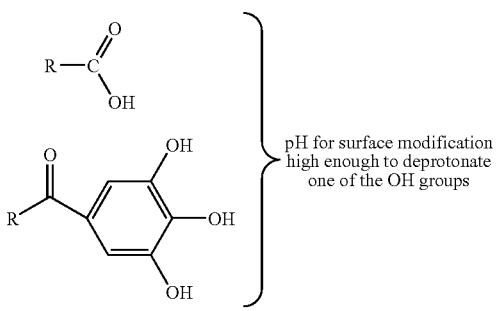

pH for surface modification high enough to deprotonate one of the OH groups

TABLE 1-continued

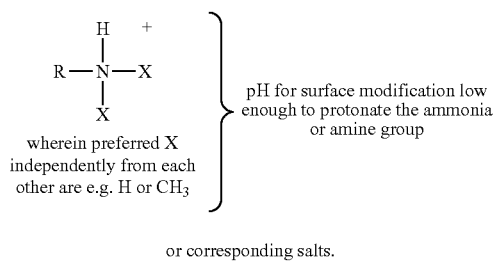

pH for surface modification low enough to protonate the ammonia or amine group wherein preferred X independently from each other are e.g. H or CH₃ or corresponding salts.

Dependent on the charge of the surface to be coated either a negatively charged headgroup is chosen or a positively charged headgroup. For e.g. $Al_2O_3$, a negatively charged headgroup is suitable at low pH conditions, i.e. pH lower than the isoelectric point, here pH<9, in particular pH 4-5. The above mentioned headgroups and further similar groups can be used to modify a broad variety of particles, in particular small particles such as metal oxides, salts and metals.

Due to the high solubility and critical micelle concentrations of the short amphiphiles, a high overall particle surface area can be covered before insoluble micelles and clusters are formed. Therefore, an enormous number of surface-modified particles can be produced within the foam liquid media and used as stabilizers of the gas-liquid interface.

Surface modification can be achieved through the physical or chemical adsorption of negatively or positively charged amphiphile molecules onto a suitable, preferably an oppositely charged surface leaving the hydrophobic tail in contact with the aqueous phase. For e.g. positively-charged alumina particles the adsorption may be carried out with carboxylic acids in water at pH 4.75. By changing the anchoring polar group of the amphiphile, the alumina surface can also be modified at alkaline pH conditions using for instance alkyl gallates as adsorbing molecule. This amphiphile can also be used to lyophobize the surface of a variety of metals and other amphoteric and basic oxides. Alternatively, the surface of acidic-like oxides such as silica, silicon carbide and silicon nitride can be lyophobized employing amine-based amphiphiles.

For the in-situ lyophobization of particles, the amphiphile is in general applied in amounts of less than 1% by weight referred to the weight of the particles, preferably in amounts of <0.8% by weight. The minimal amount of amphiphile that should be present, in general is about 0.001%, preferably about 0.1%. Since the amphiphile—besides of other ingredients of the suspension—also influences the viscosity within the above limits, the actual amount of modifier used is chosen dependent on the desired final viscosity.

For some aspects of the present invention it is also possible to use per se hydrophobic particles, e.g. Teflon (polytetrafluoroethylene) or PVDF (polyvinyldifluoride) particles. Such particles need not be surface modified, but can be directly used in combination with solvents suitable to tune the particle lyophobicity such as e.g. water supplemented with a hydrophilic solvent, such as water/alcohol mixtures or water/glycol mixtures, in particular water/ethanol mixtures.

Further partially lyophobic/lyophobized particles can be obtained by incorporating hydrophilic groups or groups suitable to be coupled to hydrophilic groups into a polymer or polymer mixture that without said groups would result in the formation of hydrophobic particles.

Such particles can e.g. be made of polymeric core beads, e.g. beads of polystyrene, polymethyl methacrylate PMMA, with surface attached carboxylate or sulfonate groups.

It has been found that partially lyophobic/partially lyophobized particles with much different shapes can be used as foam stabilizers, i.e. particles that are spherical, polygonal plates, needles, fibres, rods, single crystals etc., provided that their particle size is within suitable dimensions. In addition, the particles themselves can be dense or porous or mixtures of dense and porous particles.

The mean particle size (measured for the largest dimension) can go up to 100 μm for fibres and needles. In general, however, the mean particle sizes for all shapes are from 20 μm to 1 nm, preferably from 10 μm to 5 nm, more preferably from 2 μm to 10 nm.

It has also been found that the particle size distribution is of less importance. Good foams can be obtained with narrow as well as with broad particle size distributions.

The partially lyophobic or partially lyophobized particles are present in amounts of at least about 1% by volume referred to the volume of the suspension, preferably at least about 2% v/v, more preferred at least about 3% v/v, and still more preferred at least about 5% v/v. The upper limit is provided by the viscosity that must not be too high. In general said viscosity should not exceed 10 Pa·s at a shear rate of 100 $s^{-1}$. Slightly higher viscosities might be acceptable if very strong foaming apparatuses are available. The minimal amount needed to foam the whole suspension depends on the particle size and can easily be determined by the skilled person. In general the rule applies that the smaller the particles are, the lower the minimally needed amount is.

The nature of the particles present will depend on the intended end use of the foam to be formed. It may be one or more of the following exemplary materials: alumina, mullite, silicon carbide, silicon nitride, boron nitride, boron nitride, boron carbide, cordierite, silicas, zirconia, spinels, hydroxyapatite, calcium phosphates, in particular tri-calciumphosphate, cerium-gadoliniumoxide, magnesia and other metal oxides, e.g. tin oxide, titanium oxide and cerium oxide, or metal salts, e.g. nickel nitrate, nickel carbonate and the like, metals and alloys, such as ferrochrome, ferrosilicon, polymers, such as polyethylene, polytetrafluorethylene, polyvinylidenedifluoride. Multi-component compositions comprising mixtures of two or more of the above mentioned compounds of the same or different kind may also be used.

As continuous phase, said liquid medium comprises a solvent selected from the group comprising water, a hydrophilic solvent such as alcohols, glycols, etc. and mixtures thereof. Further additives can be added e.g. to adjust the pH, the ionic strength etc.

As already mentioned above, the preferred pH or pH range is dependent on the headgroup used for in-situ lyophobization and the particle surface to be modified. It should be such that at least about 1.5%, preferably at least about 10%, much preferred about 50% of the headgroups are negatively charged (deprotonated) or positively charged (protonated).

The ionic strength can be adjusted to favour the close-packing of the attached particles at the interface and the attraction of particles within the foam lamella. However, the ionic strength should be kept low enough to ensure sufficiently low viscosity of the suspension to allow sufficient introduction of air or good foaming, respectively, with the available apparatus.

According to the present invention, a suspension consisting of
(a) water and/or one or more hydrophilic solvents,
(b) (i) initially hydrophilic particles together with a hydrophobizing surface modifier and/or in-situ partially hydrophobized particles, (ii) initially hydrophobic particles together with a hydrophilizing surface modifier and/or partially lyophilized particles,
(iii) initially hydrophobic particles in a medium where the surface tension is adjusted to adjust the particle hydrophobicity (e.g. water/ethanol mixtures),
(iv) initially inherent partially hydrophobic particles, or
(v) combinations of two or more of (i) to (iv),
(c) optionally an acid or base to adjust the pH
(d) optionally an ionic strength influencing agent
wherein the particles are present in amounts of at least about 1% v/v referred to the volume of the suspension, preferably about 2% v/v, more preferred about 3% v/v, most preferred about 5% v/v,
is foamable and stable.

It is, however, also within the scope of the present invention, to supplement such foamable and stable suspension with further additives such as polymers, surfactants, monomers (optionally together with a polymerization initiator or an active or latent curing agent), cement, chemicals suitable to release a gas under specific conditions such as $H_2O_2$ or $N_2$-releasing additives, or other ingredients known for foams.

The viscosity of the suspension preferably is such that the viscosity is less than the level at which the introduction of gas cannot take place and above the level at which entrapped gas bubbles will tend to escape.

The critical viscosity of the suspension, in general, will be in the range of from about 5 mPa·s. to about 1000 mPa·s at a shear rate of 100 $s^{-1}$, preferably 25 mPa·s to about 1000 mPa·s. The preferred range is dependent on the method of gas entrapment. For entrapment by mechanical means e.g. stirring, the preferred range is 25 mPa·s to about 200 mPa·s.

The dispersed phase in general is a gas, in particular air. The same kind of stabilization, however is also applicable to stabilize dispersed hydrophobic liquid phases. Such hydrophobic liquid phases are e.g. fats or oils or fats and/or oils comprising phases having e.g. essential substances incorporated therein.

The foam can be prepared using different methods, for example by incorporating bubbles into the suspension. The incorporated bubbles may be small bubbles, or they may be big bubbles that upon shearing of the suspension are divided into the desired amount of small bubbles.

The bubbles of gas may be introduced in any convenient way. For convenience and economy the gas is air. Preferred methods of introduction include:

1. Subjecting the suspension to a high intensity and/or high speed agitation while exposed to the atmosphere. The agitation is preferably carried out using a mixer, e.g. a mechanical mixer rotated at high speed. The agitation is carried out for a sufficient period to introduce bubbles of air into the dispersion until expansion has been achieved according to the desired physical and other properties of the end product. The expansion ratio, i.e. the volume of foam formed compared to the volume of the starting suspension, can be between about 1.5 and about 11, preferably between about 2 and about 7. The foaming of the dispersion may also be judged visually, i.e. because the foamed composition takes on the appearance of a meringue when sufficient air has been introduced. Other gases which can be introduced include nitrogen, oxygen, argon and carbon dioxide;

2. The gas may be introduced by bubbling the gas through a filter of a defined pore size into the suspension while being stirred. In this case the final pore size of the foam may be dependant on the pore size of the filter;

3. In a variation, high pressure gas is forced through a fine filter, then intimately mixed with the suspension in a suitable chamber and the aerated mixture is then ejected from a nozzle;

4. The aerosol method may also be used, in this case the suspension is housed in a pressurized vessel and gas is injected under pressure into the suspension to produce a foam when ejected via a nozzle;

5. In another technique, a reactive gas generating substance may be added to the suspension, the substance being selected to react with acid or alkali present with the suspension to produce the required gas in-situ, either when included or when subjected to agitation or heating.

The method for preparing foams of the invention is further characterized by the following steps:
a) forming a suspension comprising as continuous phase water and/or one or more hydrophilic solvents, and as dispersed phase
(i) initially hydrophilic particles together with a hydrophobizing surface modifier and/or in-situ partially hydrophobized particles,
(ii) initially hydrophobic particles together with a hydrophilizing surface modifier and/or partially hydrophilized particles,
(iii) initially hydrophobic particles in a medium where the surface tension is adjusted to adjust the particle hydrophobicity (e.g. water/ethanol mixtures,
(iv) initially inherent partially hydrophobic particles, in particular a suspension as defined above, or
(v) combinations of two or more of (i) to (iv),
b) introducing gas into the suspension until the whole suspension is homogeneously foamed; and, if a solid article shall be made,
c) removing the liquid carrier to provide a solid article having pores derived from the bubbles, and, optionally,
d) strengthening the structure e.g. by heat treatment up to the melting point or the glass transition temperature or by sintering,
wherein the suspension has a critical viscosity selected to be below the level at which the introduction of gas cannot take place and above the level at which entrapped gas bubbles will tend to escape.

Using partially lyophobized or inherent partially lyophobic particles as foam stabilizers allows the production of foams with an air content of up to 95%, in general up to 90%, and preferred about 90%. The balance to 100% is provided by the suspension comprising partially lyophobic or lyophobized particles and liquid medium/phase (continuous medium/phase).

The bubble size of the wet foam is dependent on all the above parameters, in particular the viscosity, the amount of additives, the amount of particles and—provided that no gas releasing chemical alone is used—the apparatus or the apparatus dependent method parameters used to get air into the suspension. The bubble size usually ranges from 1 μm to 1 mm, preferably from 1 μm to 500 μm, more preferably from 1 μm to 50 μm.

The foamed composition may be allowed or caused to acquire sufficient wet green strength to allow it to be moved from the container or mould. If not a wet foam but a solid article is desired, the composition may be subjected to drying. This step serves the removal of the solvent.

In the case of water the drying can be carried out at below about 100° C., e.g. in an oven or using high frequency drying equipment. The drying step may be varied. For example, the drying may be done under reduced pressure to cause the foam to expand before the green strength is developed. The degree of expansion and hence the pore size of the foam will depend on the pressure selected. Drying at elevated temperature tends to cause a slight expansion of the foam. It is preferred to control the humidity during the drying step, to prevent uneven shrinkage and drying cracks, whereas, if an optional polymerisable material is present in the dispersion, this step might not need to be taken. Temperature-assisted or vacuum-assisted unidirectional drying leads to an even shrinkage of the sample without inducing stresses which would result in cracks.

As already mentioned above, the suspension may include other ingredients, e.g. ingredients which play a role at the drying stage. Examples of such ingredients include binders such as resins, e.g. polyvinylchloride, gums, cellulose, oligo and polysaccharides and polymerisable materials to increase green strength. A specific class of such additives is organic monomers such as soluble acrylates and acrylamides. The additives are preferably dissolved in deionized water or other carrier liquid or a mixture to produce a premix solution, a catalyst is added to the dispersion before foaming and an initiator after foaming. Elevated temperature can be a suitable substitute for the catalyst or both may be used together. Although the addition of binders etc. in general is not needed for the inventive foams, such additives may have advantages if high green strength after drying is desired. The body formed in the presence of binders or polymerizable materials after drying is relatively robust, and the addition of binders or polymerizable materials can be preferred when the article to be formed is of a complex shape.

In a similar way also stable emulsions can be made, namely by a method comprising the following steps:
a) forming a suspension comprising as continuous medium water and/or one or more hydrophilic solvents, and as dispersed phase
(i) initially hydrophilic particles together with a hydrophobizing surface modifier and/or in-situ partially hydrophobized particles,
(ii) initially hydrophobic particles together with a hydrophilizing surface modifier and/or partially hydrophilized particles,
(iii) initially hydrophobic particles in a medium where the surface tension is adjusted to adjust the particle hydrophobicity (e.g. water/ethanol mixtures),
(iv) initially inherent partially hydrophobic particles, or
(v) combinations of two or more of (i) to (iv),
b) introducing at least one non-polar liquid or mixtures of non-polar liquid and gas into the suspension until the whole suspension is formed into a homogeneous emulsion;
wherein the suspension has a critical viscosity selected to be below the level at which the introduction of non-polar liquid or mixtures of non-polar liquid and gas cannot take place and above the level at which optionally present entrapped gas bubbles will tend to escape and oil droplets will tend to phase separate.

Subsequent processing will depend on the nature of the intended article and the materials used; examples of suitable steps include shaping, e.g. machining, sintering at usual sintering temperatures, e.g. at 1400° C. to 1600° C. for $Al_2O_3$, impregnation of the pores with, e.g. catalysts and/or other agents. Porous articles made according to the invention can include: catalyst supports, flame supports and arresters; gas filters; airfresheners, ceramic armour; diesel particulate traps; insulation materials; artificial parts for the body; metal filters, reusable filters; liquid filters; Storage and transportation for flammable and/or toxic materials, humidity sensors, chromatography, filter candles for filtration of hot combustion gases, diaphragms, membranes, refractory separators, phase dividers and electrolytes for high temperature fuel cells.

The solidifying steps described above can also be applied to emulsions.

It is also possible to dilute wet-foams and emulsions prior to drying such that separate shells or capsules are formed, the structure of which can be conserved by appropriate drying and optional sintering.

In the case of shell or capsule production, additional additives are preferably added such as binders, surfactants, alcohols etc. to avoid collapsing of the shells or capsules.

Such shells or capsules out of particles that contain air or non-polar liquids or mixtures thereof can be made by a method comprising the following steps:
a) forming a suspension comprising as continuous medium water and/or one or more hydrophilic solvents, and as dispersed phase
(i) initially hydrophilic particles together with a hydrophobizing surface modifier and/or in-situ partially hydrophobized particles
(ii) initially hydrophobic particles together with a hydrophilizing surface modifier and/or partially hydrophilized particles
(iii) initially hydrophobic particles in a medium where the surface tension is adjusted to adjust the particle hydrophobicity (e.g. water/ethanol mixtures) or
(iv) initially inherent partially hydrophobic particles
(v) combinations of two or more of (i) to (iv),
b) introducing gas or at least one non-polar liquid or mixtures of non-polar liquid and gas into the suspension until the whole suspension is formed into a homogeneous foam or emulsion,
c) diluting the foam or emulsion by means of adding additional liquid, in particular water and/or one or more hydrophilic solvents
d) drying the shells or capsules in air or in particular by means of freeze drying, super critical drying or similar methods.

The characteristics of the end product may be varied according to the conditions under which the method is performed. Where the contents of the solids in the dispersion are low, the viscosity will be reduced but the foam stability may be affected; lower viscosity dispersions tend to yield articles of lower density, i.e. higher pore content for a given solids content. By increasing the speed of stirring when introducing the gas bubbles the article formed will have a high pore content and a finer average pore size.

The pore size of the porous article is dependent on all the above parameters, in particular the viscosity of the suspension, the amount of additives, the amount of particles and—provided that no gas releasing chemical alone is used—the apparatus or the apparatus dependent method parameters used to get air into the suspension. It usually ranges from 1 μm to 1 mm, preferably from 1 μm to 500 μm, more preferably from 1 μm to 50 μm.

Using partially lyophobized particles or inherently partially lyophobic particles as foam stabilizers allows the production of porous articles with porosities of up to 95%, in general up to 90%, and preferred about 90%.

It is a feature of the invention that in case of solid article production, in particular in the absence of optional additives, the final articles formed consist essentially of the starting refractory materials only. By using the inventive wet foams in the production of solid articles, not only the need for the presence of residual secondary materials, e.g. inorganic binders, can be avoided but also a weakening of the porous solid structure due to the decomposition of an organic additive during the sintering/firing process. Additionally, the pore size remains small due to the long-term stability in the wet state.

For many applications, the use of initially lyophilic, in particular hydrophilic instead of lyophobic, in particular hydrophobic particles is preferred since they can be easily dispersed in the liquid phase before the foaming process thereby avoiding the formation of agglomerates. The present invention made it for the first time possible to stabilize foams by using a large variety of particles thereby enabling not only foams with desired stability but simultaneously the adaptation of the chemical composition to specific desires. For example in the case of food industry, essential elements in nanoparticulate form can in desired composition be used to produce a foam. Or in the cosmetics industry for example physical UV filters can be incorporated into foams or dispersions with the benefit that they simultaneously stabilize said formulations. Alternatively, such foams can also be used as dye vehicle in textile industry, to suppress explosions or as fire extinguisher.

The high stability achieved with the inventive method enables the development of numerous new products in food and cosmetics industries, as well as in engineering, chemical and medical fields. The fabrication process of such porous materials including shells and capsules is extremely simple and inexpensive, and allows to produce porous ceramic structures with a wide range of compositions, porosity and pore size distributions that can be used as thermal and electric insulating ceramic parts, scaffolds and biomedical implants, porous electrodes for solid oxide fuel cells, as well as low dielectric constant materials for electronic applications; filters for molten metals and hot or corrosive gases; catalyst carriers; fire extinguisher.

Shells and capsules obtainable by the inventive methods can ab-initio or subsequently be loaded with a broad variety of gaseous, liquid or solid compounds, also very sensitive compounds, such as drugs, biomolecules, cells, in particular living cells, fragrances, flavors, dyes etc.

Due to the long time stability of the foams and the high air content, the method of the present invention is especially suitable to produce light weight ceramics, wherein also mixed ceramics are easily obtainable.

BRIEF DESCRIPTION OF THE DRAWINGS

The invention will be better understood and objects other than those set forth above will become apparent when consideration is given to the following detailed description thereof. Such description makes reference to the annexed drawings, wherein:

FIG. 1 illustrates the universality of the foaming method developed. The same principles can be easily extended to other types of particles, using different surface modifiers, liquid and gaseous phases.

MODES FOR CARRYING OUT THE INVENTION

Figure 1:
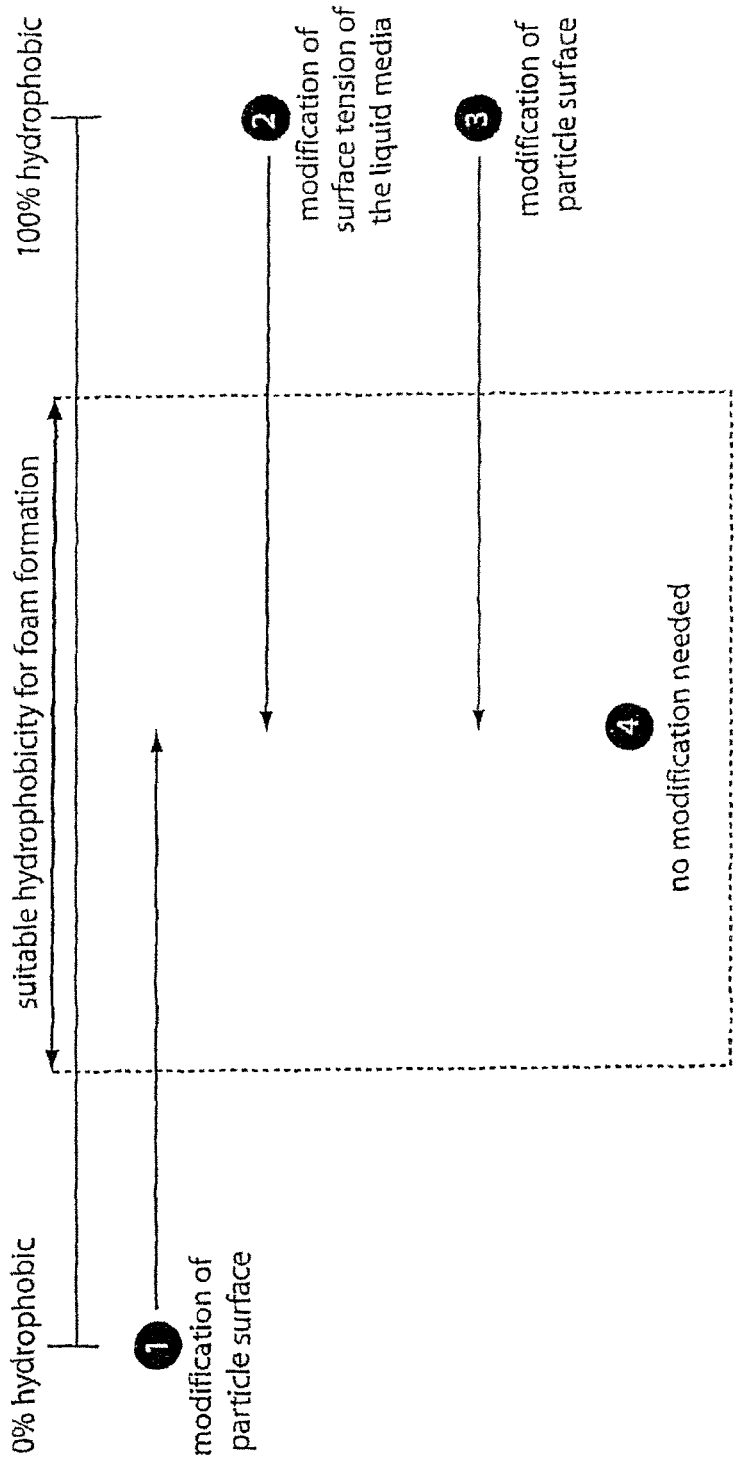
FIG. 1 is a schematic drawing of different approaches for foam formation, wherein 1-3 concern particles that are partially lyophobized either through surface modification starting from hydrophilic particles that are partially hydrophobized (1) or from hydrophobic particles the hydrophobicity of which has been reduced (3) or through the modification of the surface tension of the liquid media (2), and (4) concerns particles that are per se partially lyophobic and need no modification.

In FIG. 1, the different methods to arrive at partially lyophobic/partially lyophobized or partially hydrophobic/partially hydrophobized particles is illustrated. The numeral 1 designates the modification starting from initially lyophilic/hydrophilic particles that—due to the reaction with a surface modifier, e.g. an amphiphile, are rendered less hydrophilic or that are partially lyophobized/hydrophobized. Numeral 3 designates the modification starting from the opposite direction, i.e. the modification starting from initially lyophobic/hydrophobic particles that—due to the reaction with a surface modifier are rendered less hydrophobic or that are partially lyophilized/hydrophilized. Numeral 2 refers to the modification starting from initially lyophobic/hydrophobic particles in a medium where the surface tension is adjusted to adjust the particles lyophobicity, and numeral 4 refers to particles that are initially inherent partially lyophobic/hydrophobic particles and need no modification.

In the following description, the invention is further described based on one kind of hydrophilic particles, namely alumina particles. However, ultrastable high-volume foams containing a variety of metal oxide particles and different short amphiphilic molecules have been prepared using the below further described novel approach. This approach thus is by no means limited to the examples herein described. New foam formulations using other particles and other surface modifiers, in particular amphiphiles, can be prepared applying the concepts outlined above and here.

Aqueous foams containing alumina submicron-sized particles and a series of short-chain carboxylic acids were chosen as a model particle-amphiphile system to illustrate the new method.

The primary requirement for foam formation is the attachment of particles to the gas-liquid interface. It has been found that this can be achieved by deliberately tuning the wetting properties and the lyophobicity of the particle surface. A contact angle of 20° to 90° has proved to be in general suitable. The examples herein described illustrate the universal nature of the method, which in principle can be extended to any type of particles regardless their initial wetting behavior.

Figure 2:
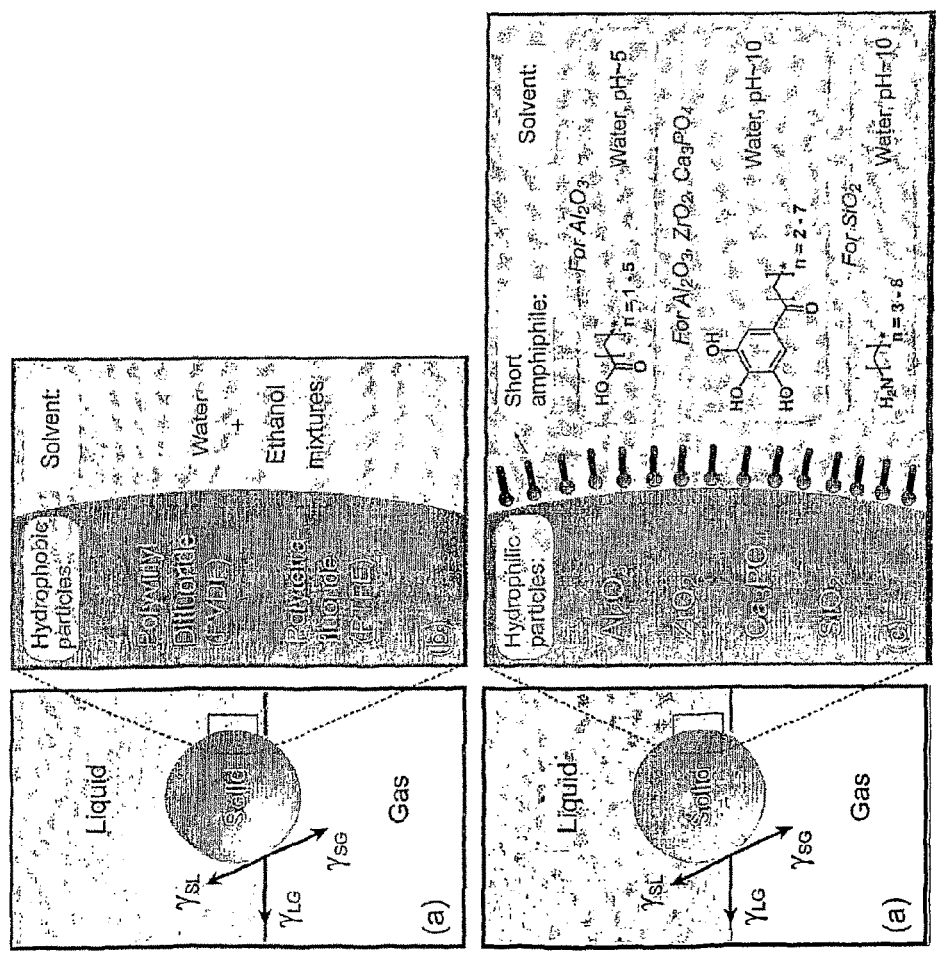
FIG. 2 shows possible approaches to tune the wetting properties and the lyophobic nature of colloidal particles, wherein
(a) shows the adsorption of partially lyophobic particles at the gas-liquid interface, illustrating the tension (γ) balance responsible for particle attachment,
(b) shows the approaches used to tune the wetting properties of originally hydrophobic particles and hydrophilic particles to illustrate the universality of the foaming method developed.
and (c) shows the approaches used to tune the wetting properties of partially hydrophobized, initially hydrophilic particles.

In general, the surface of synthetic and natural colloidal particles is often either predominantly hydrophilic or hydrophobic in nature. Hydrophilic particles (e.g. oxides) are completely wettable in water, as opposed to the non-wetting features of typically hydrophobic particles (e.g. polymers and fats). In order to tune the particle hydrophobicity and induce their adsorption at air-water interfaces, wetting on hydrophilic particles has to be diminished, whereas wetting on hydrophobic particles ought to be enhanced. FIG. 2 shows some of the approaches used as examples of how the wetting properties of typically hydrophobic and hydrophilic particles can be tuned in order to favor their adsorption at the gas-liquid interface.

Partial wetting of originally hydrophobic particles can be achieved by adjusting, for instance, the composition of the liquid aqueous phase using water/alcohol mixtures (FIG. 2(b)). Alternatively, polar or ionizable groups can be physically or chemically grafted on the particle surface to partially enhance its wettability in water.

For hydrophilic particles, on the other hand, partial surface hydrophobization can be accomplished is through the adsorption of short-chain amphiphilic molecules on the solid-liquid interface, as illustrated in the examples shown in FIG. 2(c). By choosing appropriate anchoring groups and pH conditions, a wide variety of particles can be surface hydrophobized through the adsorption of short amphiphiles via electrostatic interactions and ligand exchange reactions. Hydrophobization occurs due to the relatively strong interaction between the anchoring group and the particle surface, leaving the amphiphile hydrophobic tail in contact with the aqueous solution. This approach resembles that applied for the separation of micron-sized to millimeter-sized ore particles in flotation processes, using amphiphiles containing typically more than 10 carbons in the hydrophobic tail [15]. It is important to note that in the case of submicron sized colloidal particles in concentrated suspensions, the high total surface area of solids requires the use of amphiphilic molecules that exhibit high solubility and critical micelle concentrations in the aqueous phase in order to impart a substantial coverage of the particle surface. Therefore, molecules with typically less than 8 carbons on the hydrocarbon tail were employed for surface hydrophobization. Alternatively, partial hydrophobicity can also be imparted by chemically attaching alkyl silanes on the particle surface [8, 9, 14].

Figure 3:
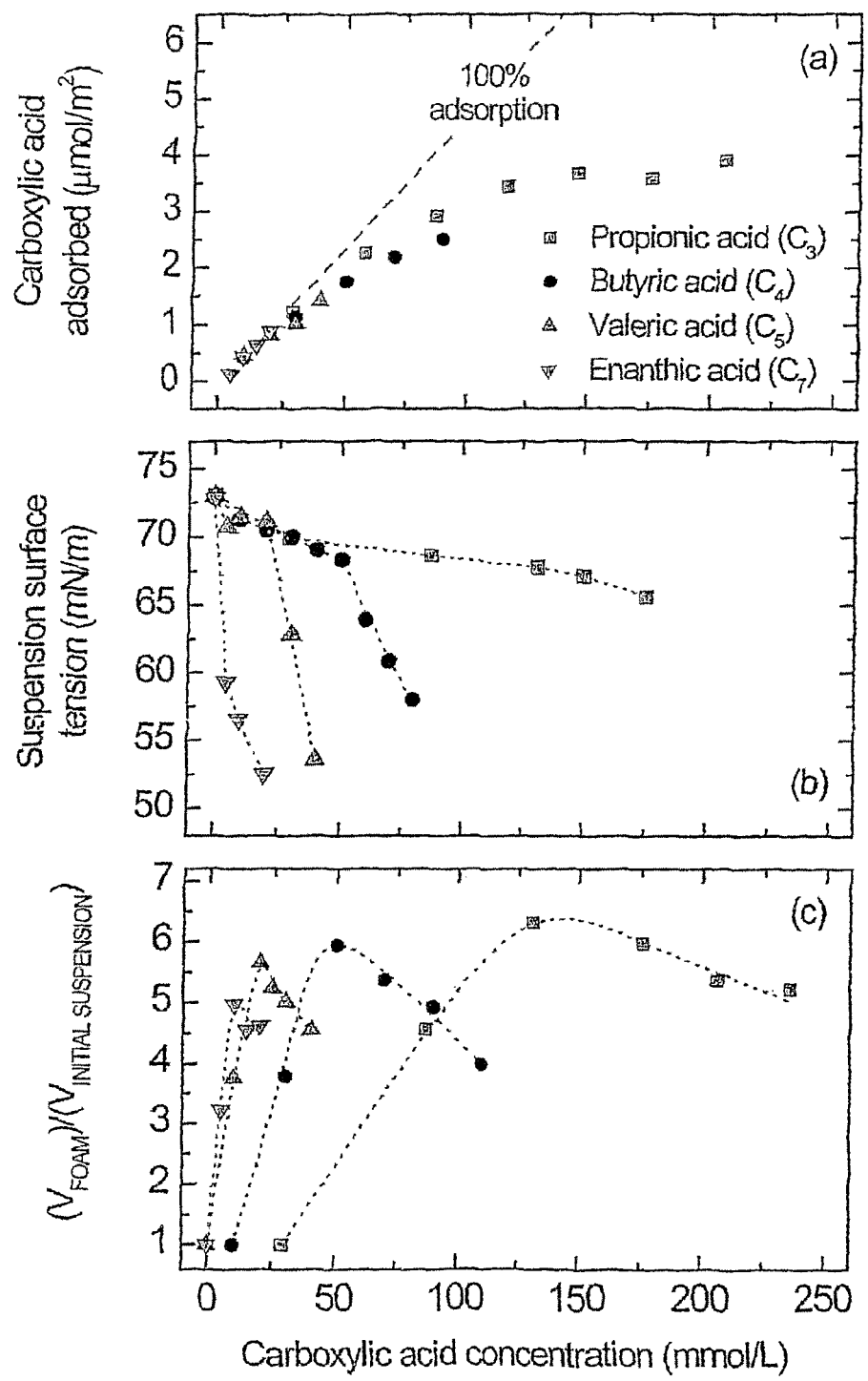
FIG. 3 shows an example of surface lyophobization using different surface modifiers, liquid and gaseous phases, and foaming behavior using alumina particles and short fatty acids as amphiphiles, wherein all data were obtained from 35 vol % alumina suspensions at pH 4.75, and wherein
(a) shows the surface lyophobization of colloidal particles accomplished through the electrostatic-driven adsorption of negatively-charged carboxylic acids on positively-charged alumina particles,
(b) shows the ability of lyophobized particles to attach at air-water interfaces which results in a significant decrease in the surface tension of colloidal suspensions, and
(c) shows that such decrease in surface tension resulted in remarkably high foamability upon high mechanical shearing.

FIG. 3(a) shows an example of the electrostatic-driven adsorption of anionic carboxylate amphiphiles onto positively-charged alumina particles in water at acidic pH conditions (FIG. 2(c)). The hydrophobization achieved via amphiphile adsorption was confirmed by contact angle measurements of valeric acid aqueous solutions (0.05 mol/L; pH=4.75) deposited on polycrystalline alumina substrates, which rendered angles of approximately 60° measured through the aqueous phase. The attachment of the resulting partially hydrophobic particles at an air-water interface was indirectly evidenced by surface tension measurements of a suspension droplet at various concentrations of added amphiphilic molecules (FIG. 3(b)). The gradual decrease in surface tension observed at lower amphiphile concentrations is caused by the adsorption of free bulk amphiphilic molecules at the gas-liquid interface. Higher amphiphile concentrations, on the other hand, led to a steep reduction of surface tension as a result of the adsorption of the coated particles at the interface. The adsorption of hydrophobized particles into the air-water interface was also evidenced by the formation of a thin stiff skin on the surface of these suspensions.

Extensive surface lyophobization may however lead to strong coagulation between particles within the liquid media. Coagulation results from the action of van der Waals and hydrophobic attractive forces among partially lyophobized particles. Although the exact origin of surface hydrophobic forces is still a matter of controversy in the literature [16, 17], the hydrophobic attractive effect has been clearly demonstrated in both flat and curved surfaces [16, 18, 19]. In the case of charged particles, repulsive Derjaguin, Landau, Vervey and Overbeek (DLVO) forces can to some extent prevent strong coagulation, aiding the incorporation and dispersion of particles into the colloidal suspension prior to the foaming process.

The low surface tension achieved via the adsorption of hydrophobized particles at the air-water interface (FIG. 3(b)) enables the preparation of foams by simply incorporating air bubbles through mechanical shearing, internal gas expansion or gas-releasing chemical reactions within the colloidal suspension. Foams prepared by vigorous mechanical shearing of concentrated alumina suspensions (35 vol % solids), for instance, showed a fivefold to sixfold increase in volume at optimum concentrations of carboxylic acid, as illustrated in FIG. 3(c). This volume increase corresponds to an amount of incorporated air of approximately 85% with respect to the total foam volume. A bubble size distribution ranging typically from 10 to 100 µm is formed via this foaming process at maximum foamability conditions. Narrower bubble size distributions are achieved by increasing the particle hydrophobicity. Further increase of the surface hydrophobicity leads, however, to extensive particle coagulation in the suspension, hindering the foaming process. This general foaming behavior was observed for all the examples outlined in FIG. 2. The surprisingly high foamability achieved with this new approach in comparison to previous investigations on particle-stabilized bubbles [8-10, 14, 20] is related to the proper tuning of some key aspects involved during the process of foam formation as outlined herein.

Foam formation is a dynamic non-equilibrium process which depends strongly on the kinetics of the diffusion-limited adsorption of surface active species on the air-water interface. High-volume foams are typically obtained when the time needed for the diffusion of surface active species to the interface is shorter than the lifetime of freshly created bubbles. The time required for particles to adsorb on the bubble surface can be reduced by increasing the particle diffusion coefficient or by decreasing the distance between the particle and the air-water interface. According to the Stokes-Einstein relation, the diffusion coefficient is inversely proportional to the particle size. The particle-interface distance, on the other hand, is inversely proportional to the number concentration of particles in the aqueous media. Based on these considerations, foam formation is favored by increasing the concentration of particles or decreasing the size of adsorbing particles. During foaming, the coagulation of single particles into clusters can markedly increase the diffusion time to the bubble surface, due to an increase of the size and a reduction of the number concentration of surface active species. Since particle coagulation is favored with the increase of surface hydrophobicity, extensive hydrophobization hinders foam formation due to the build-up of massive particle clusters in the aqueous phase, as recently outlined by Dickinson et al. [9]. High surface hydrophobicity and low concentration of particles (<2 vol %) were probably the reasons for the limited foamability achieved in previous investigations on particle-stabilized air bubbles [8-10, 20]. Even though particles exhibiting contact angle close to 90° lead to a favorable irreversible adsorption at air-liquid and liquid-liquid interfaces [14], the results shown here indicate that enhanced foamability is achieved using high concentrations of slightly hydrophobized particles which do not extensively coagulate in the aqueous phase and are thus able to promptly adsorb on the air bubble surface. For the particle size used in the example reported in FIG. 3 (diameter~200 nm), a minimum colloid concentration of 15 vol % was necessary to obtain relatively stable high-volume foams. However, this lower concentration limit could be reduced to approximately 5 vol % by using highly mobile partially-hydrophobized nanoparticles (diameter~30 nm) as foam stabilizers.

Figure 4:
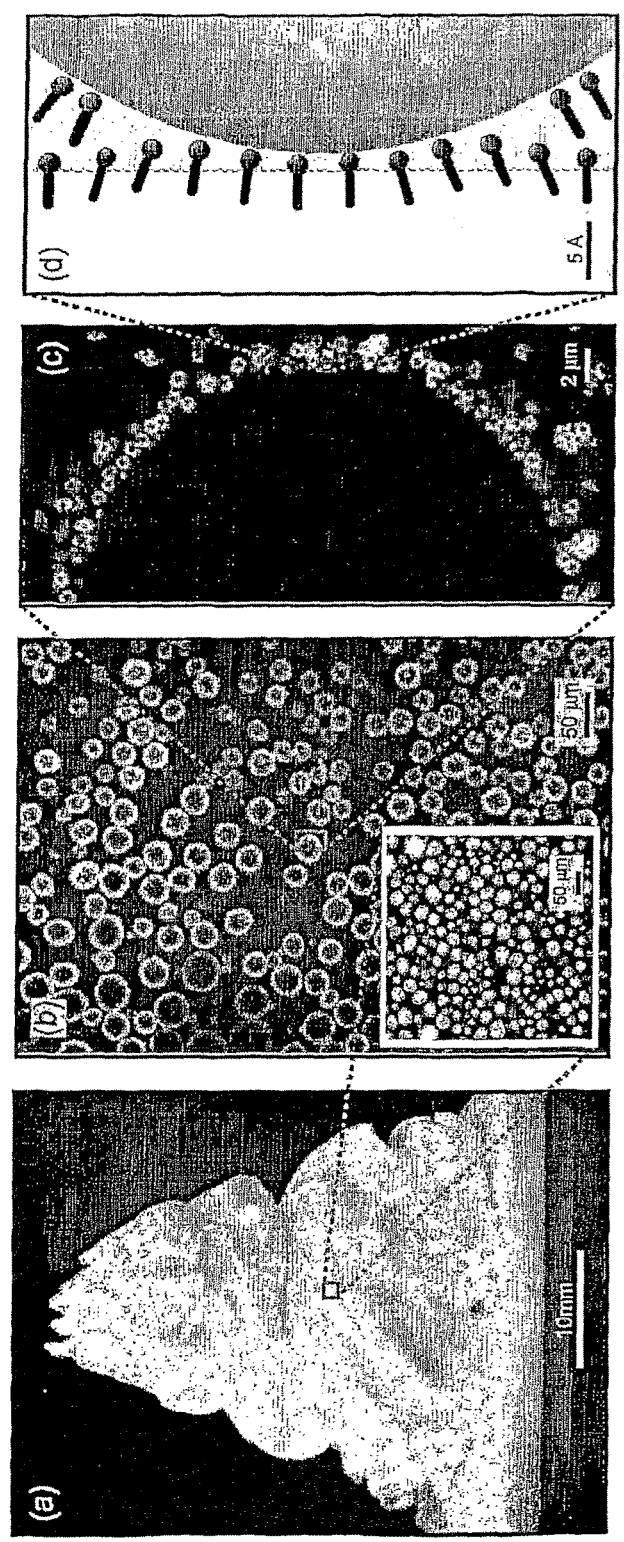
FIG. 4 shows the hierarchical features of the particle-stabilized foams containing short amphiphilic molecules. High-volume macroscopic foams (a) with bubble size within the range 10-50 μm (b) are formed through the adsorption of submicron-sized colloidal particles at the air-liquid interface (c). A possible arrange of the colloidal particles and amphiphilic molecules at the air-water interface is schematically illustrated in (d) for particles partially covered with the amphiphiles. The confocal images shown in (b) and (c) were obtained after dilution of concentrated foams (inset in b) containing fluorescently-labelled silica particles and hexyl amine as amphiphile.

The adsorption of hydrophobic particles at the air-water interface of the inventive foams was confirmed by confocal microscopy images of air bubbles obtained from the dilution of concentrated fluorescent silica foams. An enormous number of extremely stable air bubbles or hollow colloidosomes [21] were produced upon foam dilution, as shown in FIG. 4. Small clusters of particles were adsorbed at the air-water interface, suggesting the existence of an attractive colloidal network around the air bubbles. In this particular example, particles are positioned very closely to the bubble surface but apparently not pushed into the air-water interface (FIGS. 3(c) and (d)). It is quite probable that particles hydrophobized via the surface adsorption of amphiphiles, behave slightly different at the air-water interface in comparison to the idealized situation depicted in FIG. 2(a). Due to their high mobility at the particle surface, the amphiphiles may in this case accumulate on the surface area close to the neighboring air bubble, using the particles as a template for their adsorption at the air-water interface (FIG. 4(d)). This leads to a substantial decrease in surface tension without necessarily pushing the particles into the interface, as would be expected for homogeneously hydrophobized particles (FIG. 2(a)). It shall be distinctly understood that this is only a hypothesis that by no means is intended to limit the scope of the present invention.

Figure 5:
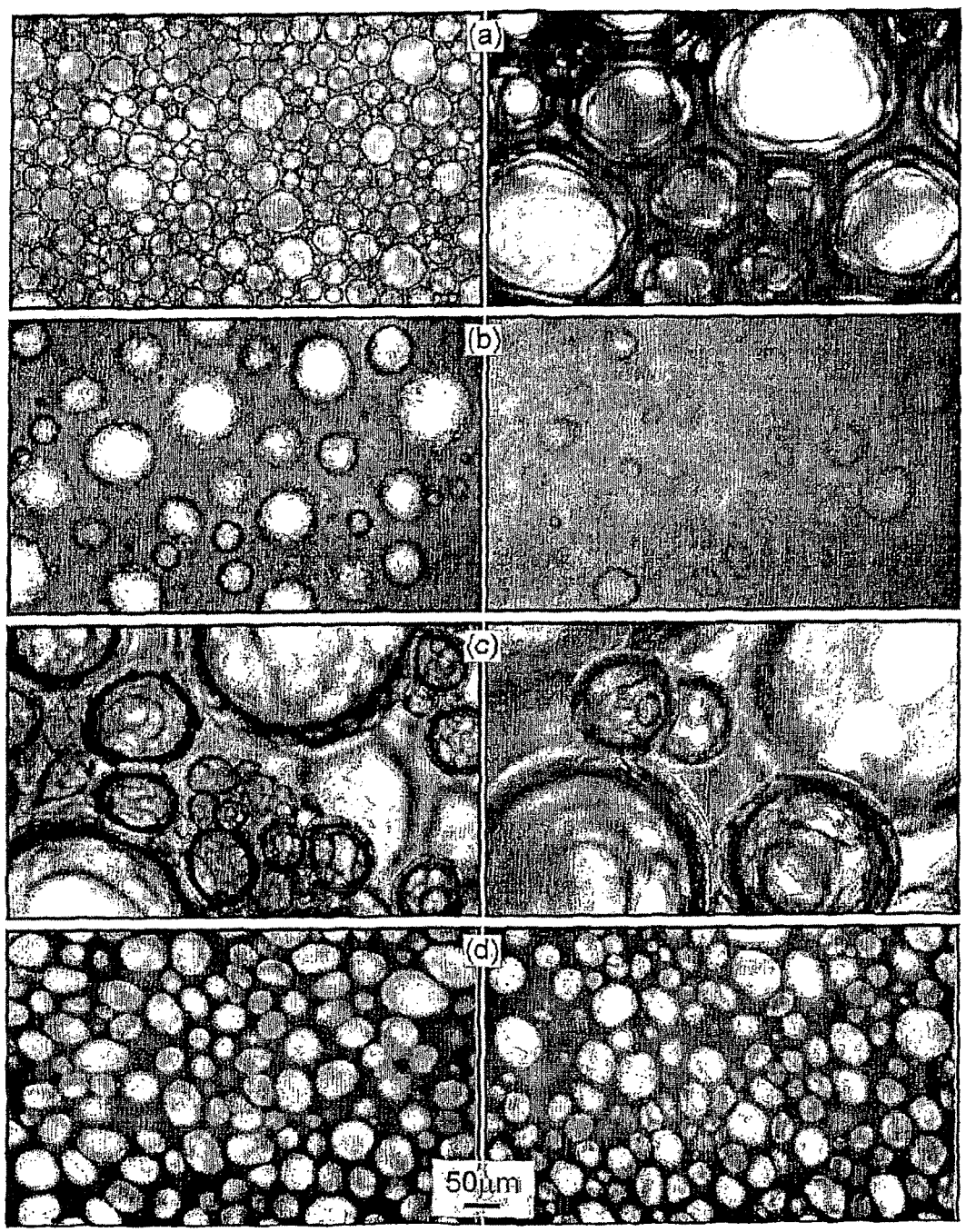
FIG. 5 shows the outstanding stability of particle-stabilized foams prepared with alumina and valeric acid at maximum foamability. No drainage and disproportionation was observed in all particle-stabilized foams prepared with partially lyophobic particles (exemplified in d), as compared to the considerable destabilization that takes place in well-established cosmetic foams (a, shaving foam) and food foams (b, whipped cream; c, egg white foam). Images shown on the left-hand side were taken 5 minutes after foaming, whereas those on the right-hand side were taken after 4 hours for the shaving (a), 69 hours for the ), whipped cream (b), 67 hours for the egg white (c) and 100 hours for the particle-stabilized foams (d). Experiments for comparison with short alkylamines adsorbed at the air-water interface and a high concentration (35 vol %) of fully hydrophilic alumina particles in the bulk phase revealed that the foam stability is not caused by the well-known approach of increasing the viscosity of the foam lamella. The same was shown in experiments with short carboxylic acids adsorbed at the air-water interface and a high concentration (35 vol %) of coagulated fully hydrophilic silica particles in the bulk phase.

The stability of the high-volume particle-stabilized foams was compared to that of foams known to be very stable in cosmetic and food applications. No liquid drainage and bubble disproportionation was observed in particle-stabilized foams within more than 4 days after foam preparation, as shown in FIG. 5. This outstanding stability contrasts to the markedly higher drainage and disproportionation rates of the evaluated food and cosmetic foams. Liquid foams containing conventional long-chain surfactants adsorbed at the air-water interface collapse much faster than the foams investigated here, typically within a couple of minutes.

Among the several mechanisms leading to foam destabilization [22], bubble disproportionation had so far been particularly difficult to avoid in liquid foams due to the ever-present difference in Laplace pressure between bubbles of distinct sizes, which ultimately results in a steady diffusion of gas molecules from smaller to larger bubbles over time [22]. The remarkable resistance of particle-stabilized foams against coalescence and disproportionation is most likely imparted by the strong attachment of particles at the air-water interface (FIG. 4) and by the formation of an attractive particle network at the interface and throughout the foam lamella.

Particles attached to the air-water interface can reduce the overall foam free energy by thousands of kTs, if a considerable amount of interfacial area is replaced upon adsorption [14, 23]. Such a reduction in free energy makes the interfacial adsorption of partially-hydrophobic particles an irreversible process, as opposed to the continuous adsorption and desorption of conventional surfactant molecules at the air-water interface (Gibbs-Marangoni effect). Particles strongly adsorbed at the interface may resist the shrinkage of small bubbles during disproportionation by forming a percolating interfacial armor that mechanically withstands the low pressures resulting from gas diffusion outwards the bubble [11]. The fact that the air bubbles are highly confined throughout the foam volume may also contribute to the enhanced stability, by restricting the movement of particles attached to the interface. In this case, the immobile attached particles would significantly hinder the mobility of the air-water interface, resembling the well-known pinning effect of particles in grain boundaries of polycrystalline materials [24].

Wet foams with remarkable long-term stability and bubble size as small as 10-100 μm can be prepared for cosmetic and food applications using the described method. The strong attachment of particles at the air-water interface also enables the fabrication of an enormous number of hollow colloidosomes for a variety of emerging applications [21]. Additionally, the outstanding foam stability allows to fabricate macroporous structures with a variety of different ceramic, polymeric and metallic materials by drying and heat treating the wet foams. Macroporous materials prepared by this simple and straightforward method can be used as low-weight structural components, porous media for chemical and biological separation, thermal and electrical insulating materials, catalyst supports, refractory filters for molten metals, and scaffolds for tissue engineering and medical implants [25-27]. Therefore, this novel technique aids the development of new products in a wide number of areas, including food, cosmetics, engineering, biology and medicine.

In the following text some Examples of wet particle-stabilized foams and emulsions are given, as well as Examples for the production of dried and sintered porous articles:

EXAMPLE I $Al_2O_3$ Foam at Acidic pH

A slurry comprising 50 vol % alumina powder (Ceralox) with a mean particle size of 200 nm was prepared by adding the powder stepwise to a solution containing water and 2.8 wt % 2N HCl (to alumina). Homogenization took place on a ballmill during 20 hours.

After ballmilling, short-chain carboxylic acids (tail length between 2 and 6 carbons) were added to the suspension and the pH was set to 4.75 with either 2N HCl or 1N NaOH. The desired solids loading (typically 35 vol %) was achieved by diluting the suspension with additional water.

This suspension was then mixed with a Kenwood kitchen mixer for 3 min (1 min at speed 4 and 2 min at maximum speed) to obtain the foam.

Investigation on the appearance and the behaviour of these foams are shown in FIG. 5, wherein FIG. 5 shows a typical light microscope image of a wet alumina foam.

EXAMPLE II $Al_2O_3$ Foam at Basic pH

A slurry comprising 50 vol % alumina powder (Ceralox) with a mean particle size of 200 nm was prepared by adding the powder stepwise to a solution containing water and 29 mmol/l propyl gallate. Homogenization took place on a ballmill during 20 hours. After ballmilling, the propyl gallate concentration was adjusted to 100 mmol/l and the pH was set to 9.8 with either 2 N HCl or 1 N NaOH. A solids loading of 35 vol % alumina was achieved by diluting the suspension with additional water.

This suspension was then mixed with a Kenwood kitchen mixer for 5 min (1 min at speed 4 and 4 min at maximum speed) to obtain the foam.

EXAMPLE III $SiO_2$ Foam

A slurry comprising 50 vol % silica powder (Nissan) with a mean particle size of 70 nm was prepared by stepwise adding the powder to the water. Homogenization took place on a ballmill during 40 hours. After ballmilling, 66 mmol/l hexylamine was added and the pH was set to 9.8 with either 2N HCl or 1N NaOH. A solids loading of 35 vol % was achieved by adding water. The suspension was then mixed with a Kenwood Kitchen Mixer during 1 min at speed 4 and 2 min at the maximum speed to obtain the foam.

EXAMPLE IV $ZrO_2$ Foam

A slurry comprising 50 vol % zirconia powder (Tosho) with a surface area of 15.2 $m^2/g$ and 100 mmol/l propyl gallate was prepared by stepwise adding the powder to a solution of water and propyl gallate. Homogenization took place on a ballmill during 20 hours. After ball milling, the pH was set to 9.8 with 2N HCl. A solids loading of 20 vol % was achieved by adding water. The suspension was then mixed with a Kenwood Kitchen Mixer during 1 min at speed 4 and 6 min at the maximum speed to obtain the foam.

EXAMPLE V $Ca_3PO_4$ Foam

A slurry comprising 10 vol % tri-calcium phosphate (TCP) with a surface area of 33 $m^2/g$ and 150 mmol/l propyl gallate was prepared. The pH was set to 9.5 with 4 N NaOH. The suspension was then mixed with a Kenwood Kitchen Mixer during 1 min at speed 4 and 6 min at maximum speed to obtain the foam.

EXAMPLE VI $Ce_{0.8}Gd_{0.2}O_2$ Foam

A slurry comprising 10 vol % $Ce_{0.8}Gd_{0.2}O_2$ (CGO20) with a mean particle size of 500 nm and 15 mmol/l valeric acid was prepared. The pH was set to 4.75 with either 2 N HCl or 1 N NaOH. The suspension was then mixed with a Kenwood Kitchen Mixer during 1 min at speed 4 and 2 min at maximum speed to obtain the foam.

EXAMPLE VII $Al_2O_3$/Octane Emulsion

A slurry comprising 50 vol % alumina powder (Ceralox) with a mean particle size of 200 nm was prepared by adding the powder stepwise to a solution containing water and 2.8 wt % 2 N HCl (to alumina). Homogenization took place on a ballmill during 20 hours. After ballmilling, 131 mmol/l propionic acid was added to the suspension and the pH was set to 4.75 with either 2 N HCl or 1 N NaOH. A solids loading of 35 vol % was achieved by diluting the suspension with additional water. Octane was then added to the suspension to achieve a concentration of 80 vol % of oil. This mixture was emulsified by mixing it with a Kenwood Kitchen Mixer during 1 min at speed 4 and 3 min at maximum speed.

EXAMPLE VIII

Polyvinylidene Fluoride Foam

Polymer particulate material (Polyvinyliden Fluoride) with MW 140 000 was mixed with water/ethanol mixture (85/15). A solids loading of 15 wt % was achieved. The suspension was mixed with a Kenwood Kitchen Mixer during 1 min at speed 4 and 6 min at the maximum speed to obtain the foam.

EXAMPLE IX

Foam from Partially Hydrophobized Silica Particles

Partially hydrophobized silica particles ($SiO_2$ HDK H30, 250 $m^2/g$, 50% SiOH on the surface) were mixed with water containing 5 vol % of ethanol. A solids loading of 5 wt % was achieved. The suspension was mixed with a Kenwood Kitchen Mixer during 1 min at speed 4 and 6 min at the maximum speed to obtain the foam.

Example of Porous Ceramics from Wet Particle-Stabilized Foams

Foams were produced as described in example I.

Drying of the Wet Foams

The high stability of the wet foams allows for long drying times. Therefore, different methods can be used to dry the wet foams:

freeze drying drying in air unidirectional drying on a hot plate (80° C.) under controlled environmental conditions (air temperature: 28° C., humidity: 80%)

unidirectional drying on a porous gypsum mold under vacuum slip casting in a porous gypsum mold Sintering of the Dried Foams The dried foams are sintered at 1575° C. for 2 hours. The heating rate is 1° C./min, whereas the cooling rate is set to 3° C./min.

Properties of the Sintered Foams

FIG. 10 shows a picture of an alumina foam which was dried by slip casting and sintered as mentioned above resulting in a porous ceramic piece with 90% porosity.

Different properties such as the density, the pore size, the compressive strength, the thermal conductivity as well as the dielectric constant were measured and are summarized in Table 2.

TABLE 2

Properties of sintered alumina foam

| Unidirectional drying method | Density [g/cm$^3$] | Porosity [%] | Average pore size [μm] | Compressive strength [MPa] | Thermal conductivity [W/mK] | Dielectric constant [—] |
|---|---|---|---|---|---|---|
| temperature assisted | 0.438 | 89.0 | 30 | 5.42 | 2 | 1.4 |
| vacuum assisted | 0.505 | 87.3 | 20 | 16.3 | — | — |

While there are shown and described presently preferred embodiments of the invention, it is to be distinctly understood that the invention is not limited thereto but may be otherwise variously embodied and practiced within the scope of the following claims.

REFERENCES

1. Brooker, B. E., *The Stabilization of Air in Foods Containing Fat—a Review*. Food Structure, 1993. 12(1): p. 115-122.

2. Goff, H. D., *Colloidal aspects of ice cream—A review*. International Dairy Journal, 1997. 7(6-7): p. 363-373.

3. Simone, A. E. and L. J. Gibson, *Aluminum foams produced by liquid-state processes*. Acta Materialia, 1998. 46(9): p. 3109-3123.

4. Green, D. J. and R. Colombo, *Cellular ceramics: Intriguing structures, novel properties, and innovative applications*. Mrs Bulletin, 2003. 28(4): p. 296-300.

5. Padture, N. P., M. Gell, and E. H. Jordan, *Materials science—Thermal barrier coatings for gas-turbine engine apptications*. Science, 2002. 296(5566): p. 280-284.

6. Hench, L. L., *Bioceramics*. Journal of the American Ceramic Society, 1998. 81(7): p. 1705-1728.

7. Griffith, L. G. and G. Naughton, *Tissue engineering—Current challenges and expanding opportunities*. Science, 2002. 295(5557): p. 1009-+.

8. Du, Z. P., et al., *Outstanding stability of particle-stabilized bubbles*. Langmuir, 2003. 19(8): p. 3106-3108.

9. Dickinson, E., et al., *Factors controlling the formation and stability of air bubbles stabilized by partially hydrophobic silica nanoparticles*. Langmuir, 2004. 20(20): p. 8517-8525.

10. Sun, Y. Q. and T. Gao, *The optimum wetting angle for the stabilization of liquid-metal foams by ceramic particles: Experimental simulations*. Metallurgical and Materials Transactions a-Physical Metallurgy and Materials Science, 2002. 33(10): p. 3285-3292.

11. Kam, S. I. and W. R. Rossen, *Anomalous capillary pressure, stress, and stability of solids-coated bubbles*. Journal of Colloid and Interface Science, 1999. 213(2): p. 329-339.

12. Kaptay, G., *Interfacial criteria for stabilization of liquid foams by solid particles*. Colloids and Surfaces a-Physicochemical and Engineering Aspects, 2003. 230(1-3): p. 67-80.

13. Murray, B. S. and R. Ettelaie, *Foam stability: proteins and nanoparticles*. Current Opinion in Colloid & Interface Science, 2004. 9(5): p. 314-320.

14. Binks, B. P., *Particles as surfactants—similarities and differences*. Current Opinion in Colloid & Interface Science, 2002. 7(1-2): p. 21-41.

15. Moudgil, B. M., Singh, P. K. & Adler, J. J. in *Handbook of Applied Surface and Colloid Chemistry* (ed. Holmberg, K.) 591 (John Wiley & Sons Ltd., West Sussex, 2002)

16. Christenson, H. K. & Claesson, P. M. Direct measurements of the force between hydrophobic surfaces in water. *Advances in Colloid and Interface Science* 91, 391-436 (2001).

17. Parker, J. L., Claesson, P. M. & Attard, P. Bubbles, Cavities, and the Long-Ranged Attraction between Hydrophobic Surfaces. *Journal of Physical Chemistry* 98, 8468-8480 (1994).

18. Ametov, I. & Prestidge, C. A. Hydrophobic interactions in concentrated colloidal suspensions: A rheological investigation. *Journal of Physical Chemistry B* 108, 12116-12122 (2004).

19. Israelachvili, J. & Pashley, R. The Hydrophobic Interaction Is Long-Range, Decaying Exponentially with Distance. *Nature* 300, 341-342 (1982).

20. Alargova, R. G., Warhadpande, D. S., Paunov, V. N. & Velev, O. D. Foam superstabilization by polymer microrods. *Langmuir* 20, 10371-10374 (2004).

21. Dinsmore, A. D. et al. Colloidosomes: Selectively permeable capsules composed of colloidal particles. *Science* 298, 1006-1009 (2002).

22. Wilson, A. J. (ed.) *Foams: Physics, Chemistry and Structure* (Springer-Verlag, Berlin, 1989).

23. Aveyard, R., Binks, B. P. & Clint, J. H. Emulsions stabilised solely by colloidal particles. *Advances in Colloid and Interface Science* 100, 503-546 (2003).

24. Nikolaides, M. G. et al. Electric-field-induced capillary attraction between like-charged particles at liquid interfaces. *Nature* 420, 299-301 (2002).

25. Scheffler, M. & Colombo, P. (eds.) *Cellular ceramics: Structure, manufacturing, properties and applications* (Wiley-VCH, Weinheim, 2005).

26. Ashby, M. et al. *Metal Foams: A Design Guide* (Butterworth-Heinemann, Oxford, 2000).

27. Hench, L. L. & Polak, J. M. Third-generation biomedical materials. *Science* 295, 1014-+ (2002).

The invention claimed is:

1. A method of preparing wet foams exhibiting long-term stability comprising the steps of
   a) forming a suspension comprising as continuous medium water and/or one or more hydrophilic solvents and colloidal particles as a dispersed phase and
   b) introducing gas into the suspension to produce a wet foam wherein said colloidal particles are used to stabilize a gas-liquid interface and wherein the particles are present in amounts of at least about 5% by volume referred to the volume of the suspension, wherein the particles are initially hydrophilic and are in-situ lyophobized through adsorption of amphiphilic molecules on the particle surface, wherein amphiphilic molecules consist of a tail coupled to a headgroup, wherein the tail is an aliphatic $C_2$-$C_8$ (linear or branched) or cyclic (alicyclic or aromatic) optionally substituted hydrocarbon and the headgroup is an ionic group selected from phosphates, phosphonates, sulfates, sulfonates, amines, amides, pyrrolidines, gallate, carboxylic acids, and corresponding salts, and wherein the whole of the suspension is homogeneously foamed wherein the foam has a long term stability of at least one week.

2. The method of claim 1 wherein the mean particle sizes (measured for the largest dimension) are up to about 100 μm for fibers and needles.

3. The method of claim 1 wherein the mean particle sizes (measured for the largest dimension) are from 20 μm to 1 nm for all particle shapes except fibers and needles.

4. The method of claim 1 wherein the amphiphilic molecules suitable for in-situ surface hydrophobization are able to reduce surface tension of an air-water interface to values less than or equal to 65 mN/m for concentrations less than or equal to 0.5 mol/l and wherein the amphiphilic molecules have a solubility in the liquid phase of the suspension given by the following equation:

$$\text{SOLUBILITY[mol/l]} \geq m \cdot \frac{\phi}{1-\phi} \cdot \rho_{powder} \cdot S_A$$

$m = 4 \cdot 10^{-8} (T^s [\text{mol}/m^2]$ $\phi$: Solids Loading [−]

$\rho_{power}$: Density of powder [g/l]

$S_A$: Surface Area of Powder [$m_2$/g].

5. The method of claim 1 wherein the tail comprises an optionally substituted linear carbon chain of 2 to 8 carbon atoms, and the headgroup is selected from the group consisting of:

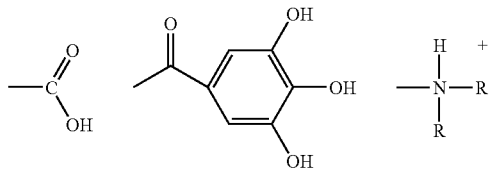

and corresponding salts.

6. The method of claim 1, wherein the pH during in-situ lyophobization is such that at least about 1.5% of the headgroups are negatively or positively charged.

7. The method of claim 1 wherein the suspension further comprises initially hydrophobic particles.

8. The method of claim 7 wherein the amphiphilic molecules suitable for in-situ surface lyophilization have a critical micelle concentration (CMC) higher than 10 μmol/l or have a solubility higher than 1 μmol/l or where the particles lyophobicity is adjusted through adjustments of the liquid medium or continuous phase.

9. The method of claim 1 wherein for the in-situ lyophobization of particles, a modifier is applied in amounts of 0.001 to 1% by weight referred to the weight of the particles.

10. The method of claim 1 wherein the particles are selected from the group consisting of oxides, carbides, nitrides, phosphates, carbonates, polysaccharides, salts, metals, polymers, fats and mixtures thereof.

11. The method of claim 1 wherein the suspension further comprises pH and/or ionic strength adjusting agents.

12. The method of claim 1 wherein the suspension further comprises additives selected from the group consisting of polymers, surfactants, monomers optionally together with a polymerization initiator or an active or latent curing agent.

13. The method of claim 1 comprising the following steps:
   a) forming a suspension comprising as continuous medium water and/or one or more hydrophilic solvents, and as dispersed phase said particles and optionally one or more of
      (i) initially hydrophobic particles together with a hydrophilizing surface modifier and/or partially lyophilized particles,
      (ii) initially hydrophobic particles in a medium where the surface tension is adjusted to adjust the particle hydrophobicity, and
      (iii) initially inherent partially hydrophobic particles
   b) introducing gas into the suspension until the whole suspension is homogeneously foamed; wherein the suspension has a critical viscosity selected to be below the level at which the introduction of gas cannot take place and above the level at which entrapped gas bubbles will tend to escape.

14. The method of claim 9, wherein the modifier is applied in amounts of 0.1 to 0.8% by weight.

15. The method of claim 1, wherein the suspension further comprises additives selected from the group consisting of reactive gas generating substances, said substance being selected to react with acid or alkali present in the suspension to produce said gas in situ.

16. The method of claim 12, wherein the suspension further comprises additives selected from the group consisting of reactive gas generating substances, said substance being selected to react with acid or alkali present in the suspension to produce said gas in situ.

* * * * *

UNITED STATES PATENT AND TRADEMARK OFFICE
CERTIFICATE OF CORRECTION

PATENT NO. : 8,975,301 B2  
APPLICATION NO. : 12/097199  
DATED : March 10, 2015  
INVENTOR(S) : Ludwig J. Gauckler et al.

Page 1 of 1

It is certified that error appears in the above-identified patent and that said Letters Patent is hereby corrected as shown below:

In the Claims:

At Column 21, line 42, "$(T^s[mol/rn^2]$" should be -- $(T^s[mol/rn^2])$ --.

At Column 21, line 45, "$\rho_{power}$:" should be -- $\rho_{powder}$: --.

Signed and Sealed this  
Fifteenth Day of December, 2015

Michelle K. Lee  
*Director of the United States Patent and Trademark Office*